United States Patent
Cookson et al.

(10) Patent No.: US 8,354,233 B2
(45) Date of Patent: Jan. 15, 2013

(54) SEQUENCE DATA BY REDUCTION OF NOISE DUE TO CARRY-OVER PRIMER

(75) Inventors: Brad T. Cookson, Mercer Island, WA (US); Dhruba J. Sengupta, Lynnwood, WA (US)

(73) Assignee: University of Washington, Seattle, WA (US)

( * ) Notice: Subject to any disclaimer, the term of this patent is extended or adjusted under 35 U.S.C. 154(b) by 130 days.

(21) Appl. No.: 12/935,977

(22) PCT Filed: Mar. 31, 2009

(86) PCT No.: PCT/US2009/039020
§ 371 (c)(1),
(2), (4) Date: Jan. 26, 2011

(87) PCT Pub. No.: WO2009/124085
PCT Pub. Date: Oct. 8, 2009

(65) Prior Publication Data
US 2011/0244452 A1    Oct. 6, 2011

Related U.S. Application Data

(60) Provisional application No. 61/072,739, filed on Apr. 1, 2008, provisional application No. 61/196,524, filed on Oct. 16, 2008.

(51) Int. Cl.
*C12Q 1/68*    (2006.01)
*C12P 19/34*    (2006.01)

(52) U.S. Cl. .......... 435/6.12; 435/6.1; 435/6.11
(58) Field of Classification Search .............. None
See application file for complete search history.

(56) References Cited

U.S. PATENT DOCUMENTS

| 2003/0148313 A1 | 8/2003 | Strathmann |
| 2007/0148645 A1 | 6/2007 | Hoser |

OTHER PUBLICATIONS

Tragoonrung et al., "Sequence-tagged-site-facilitated PCR for barley genome mapping," Theor. Appl. Genet., 1992, vol. 84, pp. 1002-1008.*
USB, Sequenase Version 2.0 PCR Products Sequencing Kit. 1999; 28 pages.
Ge et al. Thermo Sequenase Radiolabeled Terminator Cycle Sequencing Kit, 2000. 28 pages.
Sambrook et al. "Chapter 12 DNA Sequencing" Molecular Cloning, 2001, vol. 2, 4 pages.

* cited by examiner

*Primary Examiner* — Young J Kim
(74) *Attorney, Agent, or Firm* — Kilpatrick Townsend & Stockton LLP

(57) ABSTRACT

The present invention provides methods of reducing the background signal of a nucleic acid sequencing reaction. In particular, the invention provides methods of specifically degrading unwanted chain termination reaction products generated by the extension of primers carried over from the amplification step of the sequencing reaction. These methods are amenable for use with both one step and two-step amplification/chain termination reaction sequencing protocols.

22 Claims, 6 Drawing Sheets

Schematic representation of sequencing products and electropherogram at the end of combined amplification/sequencing reaction. Conventional (A) vs. SeqSharp (B)

A

B

5' OH phosphorylation      Lambda Exonuclease

Schematic representation of sequencing products and electropherogram at the end of amplification and sequencing reaction (two-steps). Conventional (A) vs. SeqSharp (B)

Electropherograms showing sequence data obtained by amplification and sequencing (two steps). Conventional (A) vs. SeqSharp (B)

Schematic representation of sequencing products and electropherogram at the end of combined amplification/sequencing reaction. Conventional (A) vs. SeqSharp (B)

● 5' OH phosphorylation   Lambda Exonuclease

Electropherograms showing sequence data obtained by combined amplification/sequencing. Conventional (A) vs. SeqSharp (B)

Electropherograms showing sequence data obtained using an equimolar ratio of amplification primers, for sequencing the forward strand (A) and reverse strand (B) of the bacterial 16S rRNA gene.

A

B

Electropherograms showing sequence data obtained using dNTP mixtures with either dGTP (A) or a 4:1 ratio of dITP:dGTP (B).

A

B

SEQUENCE DATA BY REDUCTION OF NOISE DUE TO CARRY-OVER PRIMER

CROSS-REFERENCES TO RELATED APPLICATIONS

This application is related to U.S. Ser. No. 61/072,739, filed Apr. 1, 2008, and U.S. Ser. No. 61/196,524, filed Oct. 16, 2008, both of which are herein incorporated by reference in their entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

1. Field of the Invention

The present invention is drawn to the general field of DNA amplification and sequence determination. More specifically, the present invention provides methods for lowering the background signal generated during DNA sequencing due to the carry over of primers from the amplification step. These methods are generally applicable to all known methods of DNA sequencing that rely on the amplification of the target sequence prior to delineation of the nucleotide sequence. Also included in the present invention are kits for the production of nucleic acid sequencing data with reduced background noise due to amplification primer carry over.

2. Background

The Sanger method for determining the sequence of a DNA molecule (PNAS: 74, 5463-5467 (1977)) requires a relatively large amount of purified, single-stranded DNA template. Alternatively, the cycle sequencing method (Murray, V., Nucleic Acids Res.: 17, 8889 (1989)) does not require a single-stranded template and allows the sequence reaction to be initiated with relatively small amounts of template. However, this method does require that the template DNA be purified to almost complete homogeneity. Due to this limitation, template DNA is routinely prepared by means of PCR amplification (Mullis, K. B. and Faloona, F. A., Methods Enzymol.: 155, 335-350 (1987)) when the target sequence is contained in a large mixture of DNA sequences.

In both of the above methods, DNA sequencing is accomplished by first performing an enzymatic chain termination reaction, as described by Sanger, followed by the subsequent delineation of the DNA sequence from the chain termination reaction products. First, a nucleic acid template is used to generate a plurality of labeled nucleic acid fragments of various lengths by the action of a suitable DNA polymerase. This is accomplished by hybridizing to the DNA molecule an oligonucleotide complimentary to the target sequence and extending that oligonucleotide by incorporation of deoxynucleotide triphosphates (dNTPs) in the presence of dideoxynucleotide triphosphates (ddNTPs). Commonly, these ddNTPs are labeled with, for example, a radioactive isotope, such as phosphorus 32, or a fluorescent moiety. These chain termination reaction products are then used to determine the sequence of the target, for example after polyacrylamide gel electrophoresis or capillary electrophoresis.

An important step between the amplification and chain termination reaction steps of a sequencing procedure is the removal of unused primers at the end of the amplification reaction. Incomplete removal of primers can lead to noisy and unreliable sequencing data. While enzymatic, chromatographic and ultrafiltrational methods for removing excess primers are well known in the art (Dugan et al., J. Forensic Sci., 47:811-818 (2002)) (Smith and Ballantyne, J. Forensic Sci., 52:820-829 (2007)), these methods are not always adequate to reduce the noise caused by the extension products from primers carried over from the amplification step. Laboratories that rely on the success of high-throughput DNA sequencing often encounter sequencing data that are unusable due to such noise. Recently, a method called the AmpliSeq (Murphy et al., Clin. Chem., 51:35-39 (2005)) that combines both amplification and sequencing in a single step has been described. Since the AmpliSeq method does not allow the removal of excess primers between the amplification and sequencing step, the final data can be sometimes ambiguous. Therefore, there is a need in the art for a method of reducing the background noise, post chain termination reaction, of a sequencing reaction created by the extension of primers carried over from the amplification step of the procedure. The current invention satisfies this need by providing enzymatic methods of degrading unwanted chain termination reaction products. The methods of the present invention are effective in improving sequencing data for both regular amplification followed by cycle sequencing and one-step amplification/cycle sequencing.

BRIEF SUMMARY OF THE INVENTION

The present invention provides methods of reducing the background signal of a nucleic acid sequencing reaction. Specifically, the invention provides methods of reducing the background signal of a nucleic acid sequencing reaction generated by the elongation of primers carried over from the amplification step, during the chain termination reaction step of the procedure.

In one aspect, the invention provides a means of enzymatically degrading an unwanted product generated during the chain termination reaction step of a nucleic acid sequencing reaction. In particular, the invention provides methods of degrading the unwanted products through the use of an enzyme that recognizes, or has increased substrate specificity, for a particular chemical modification contained within primers designed for the amplification step and not for the chain termination reaction step of a sequencing procedure.

In one embodiment of the invention, the chemical modification is made to the amplification primers, not intended for use as chain termination reaction primers, at the free 5'-OH of the primer. In a particular embodiment, the chemical modification is a 5' terminal phosphate. In other embodiments, the 5'-OH is modified by pyrophosphate, biotin, a methyl group, or by any other well known chemical modification in the art.

In a particular embodiment, the invention provides a method of degrading any chain termination reaction product generated by the extension of an oppositely oriented primer carried over from the amplification step of the procedure. In one embodiment, the chain termination reaction primer is the same as one of the amplification primers. In this embodiment, only the amplification primer that is different from the chain termination reaction primer is chemically modified. In other embodiments, the chain termination reaction primer, or amplification primer that is the same as the chain termination reaction primer, is chemically modified with a different modification. In this embodiment, the chemical modification made to the chain termination reaction primer, or amplification primer that is the same as the chain termination reaction primer, is not recognized by and does not confer increased substrate specificity to an enzyme used to degrade unwanted chain termination reaction products.

In another embodiment, the chain termination reaction primer is different from both of the amplification primers. In this embodiment, both of the amplification primers are chemically modified and the current invention provides methods of degrading any chain termination reaction product generated by extension from one of these primers. In another embodiment, multiple chain termination reaction primers are used. In this embodiment, any amplification primer that is not the same as any chain termination reaction primer may be chemically modified.

In another embodiment, the ratio of the concentration of the amplification primers to the concentration of the chain termination reaction primer(s) is unequal. In another embodiment of the invention, the ratio of the concentration of the amplification primers to the concentration of the chain termination reaction primer(s) is approximately equal.

In another embodiment, multiple pairs of amplification primers are used and one or more chain termination reaction primers are used. In this embodiment, any amplification primer that is not the same as any chain termination reaction primer may be chemically modified and the present invention provides methods of degrading any unwanted chain termination reaction products generated by the extension of any amplification primer that is different from any chain termination reaction primer.

In another embodiment, multiple target nucleic acid sequences are simultaneously sequenced. The present invention provides methods of reducing the background generated by the chain termination reaction-mediated extension of primers carried over from the amplification step of the sequencing reaction.

In a particular embodiment, the present invention provides methods of reducing the background generated by an unwanted chain termination reaction product generated during a sequencing reaction in which the amplification and chain termination reactions are performed at the same time. In one embodiment, the current invention provides methods of reducing the background signal in a one-step amplification/sequencing reaction. In one embodiment the one-step amplification/sequencing procedure is AmpliSeq or any other one step protocol well known in the art.

In another aspect, the invention provides methods of determining the identity of a single nucleotide at predetermined location in a polynucleotide. In certain embodiments, the methods comprise single base extension reactions using one or more sequencing primers. In one embodiment, the methods provided herein allow for simultaneous amplification and SNP genotyping at one or more loci, for example, at one or more genomic loci in an organism or a biological sample from a subject.

DETAILED DESCRIPTION OF THE INVENTION

Figure 1:
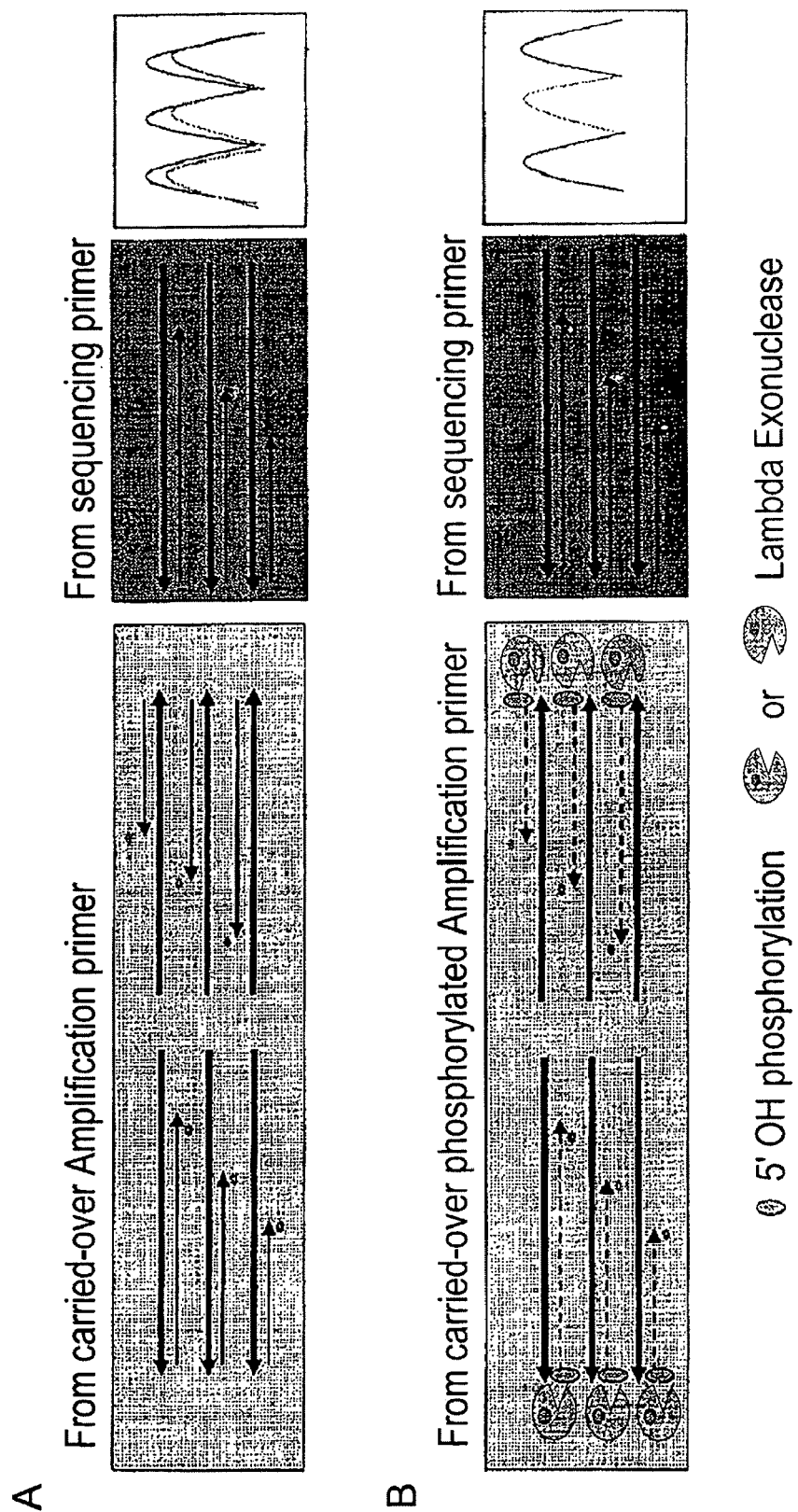
FIG. 1 A schematic diagram showing SeqSharp improves sequence quality by specific removal of tagged extension products. Panel A shows that the presence of residual amplification primers carried over to the sequencing step can lead to ambiguous sequence data. Panel B shows, by specifically removing tagged (5'OH phosphorylated) chain termination products, SeqSharp improves the sequence data.

Cycle sequencing from PCR products is a fast and convenient method that can be used for a variety of practical purposes well known in the art. A common source of noise in the sequencing data is the chain termination product that originates from the opposite strand. At present there are many methods that are used prior to performing the chain termination reaction in order to alleviate this problem, including digesting amplification products with a single strand-specific nuclease, purifying excess primer away from the products of the amplification reaction via a mini ion-exchange, silica columns, or ultrafiltration, and other methods well known in the art. All of these methods assume that excess primers are present in free single stranded form and can therefore be easily purified away from a PCR product that is double-stranded and substantially higher in molecular weight. However, primers can potentially form both inter and intramolecular structures that are dependent on salt concentration that can significantly affect the ability of these methods to separate the primers away from the PCR products.

The background noise in the sequencing data from the amplification primers can be easily and efficiently removed by methods of the present invention. One embodiment of the invention entails use of 5'-phosphorylated primers for amplification and non-phosphorylated primers for the chain termination reaction followed by a brief incubation of the chain termination reaction products with a suitable exonuclease, such as lambda exonuclease. Lambda exonuclease processively cleaves the 5'-phosphorylated strand of a duplex DNA molecule (Mitsis and Kwagh, Nucleic Acids Res., 27:3057-3063 (1999)) and can be used to produce specific single strands from double stranded DNA (Schwieger and Tebbe, Applied and Environmental Microbiology, 66(8):3556-3565 (2000); Boissinot et al., Clin. Chem., 53:2020-2023 (2007)). Other suitable exonucleases that have increased specificity for chemically modified DNA are well known in the art and are encompassed herein.

In a molecular biology laboratory, sequencing protocols generally involve a PCR mediated amplification of the target DNA that employs a forward and a reverse primer, which is followed by a sequencing reaction directed from a single primer. The sequencing reaction involves extension from a primer that is subsequently terminated by the incorporation of fluorescently labeled dideoxynucleotides. To minimize the contribution of fluorescent signal from extension products originating from the residual oppositely oriented primer that is carried over from the amplification step, an intermediate step is routinely incorporated to remove excess primers before proceeding to the sequencing reaction. Nevertheless, one often encounters sequence results where an electropherogram clearly suggests contribution from primers carried over from the amplification step. One embodiment of the present invention, a method called SeqSharp, reduces noise in the sequencing data by removing chain termination products originating from the oppositely oriented primer. This method is particularly useful in situations where removal of unused primers between the amplification and sequencing is not possible or desirable. This method substantially improves the quality of sequence information even when no intermediate primer removal step is incorporated. Furthermore, SeqSharp significantly improves the quality of sequence from a combined (one-step) amplification/sequencing protocol.

A prerequisite for traditional cycle-sequencing is efficient removal of primers, for example the oppositely oriented primers, after the amplification step. One embodiment of the present invention provides an alternative method combining amplification with sequencing that offers the potential for reducing the number of hands-on steps for sequencing a DNA template. Single-step protocols are dependent on the successful transition from the amplification phase to the sequencing phase occurring in a single reaction mixture. This transition is sensitive to the efficiency of the amplification phase for the exhaustion of the primer whose extension product during the sequencing phase can cause noise in the data. Efficiency of PCR amplification is known to be sensitive to a variety of factors such as template purity, template concentration and well to well variation within a single PCR run. These variations can prove to be a major impediment to the high throughput use of a standard single-step protocol, such as AmpliSeq.

One embodiment of the present invention significantly improves the quality of data generated by single-step protocols, such as AmpliSeq, by selectively cleaving 5'-phosphorylated polynucleotide strands. The present method can be used with any primer based sequencing system.

Advantageously, methods of the present invention employ readily available reagents such as phosphorylated primers and lambda exonuclease. Given that DNA sequencing is one of the most important steps in modern biology and diagnostic techniques, the present invention offers an alternative to the current methods which are used to remove excess amplification primers. At current market rates, methods of the present invention significantly reduce the cost of performing nucleic acid sequencing. Additionally, for laboratories that are interested in further cost saving by using a combined amplification and sequencing protocol, methods of the present invention achieve higher quality and more reliable sequence results. The present invention also achieves higher quality sequence results by using reagents that promote uniform mobility during capillary electrophoresis. Yet another advantage of the present invention is its increased simplicity, due to the fact that the DNA template does not need to be preheated before it is added to the amplification/sequencing reaction. The invention also saves time, due to the fact that the primer removal step is not required. Time and expense are also saved by having higher quality data and less need to repeat experiments.

A common problem encountered by laboratories relying on high-throughput sequencing is that the data quality is often compromised due to the extension of carried-over amplification primers during the sequencing reaction. As illustrated in FIG. 1A, presence of primers carried over from the amplification step leads to extension products from both forward and reverse primers. This leads to an ambiguous or unreliable basecalling. Even a 5-10 fold higher concentration of the sequencing primer compared to the concentration of carried over amplification primers is not always able to compensate for the noise. By specifically removing the fluorescent chain termination products originating from the excess amplification primers with the methods of the current invention, the noise in the sequence data is removed.

As such, in one aspect, the present invention provides novel methods, generally referred to as SeqSharp methods, that help substantially improve the quality of cycle sequencing data by specifically tagging a primer whose extension products are enzymatically degraded before capillary gel electrophoresis (FIG. 1B).

In a particular embodiment, the methods provided for reducing the background signal generated during a nucleic acid sequencing reaction comprise the steps of (a) amplifying a nucleic acid by an amplification reaction, for example polymerase chain reaction (PCR), with a forward and a reverse primer, wherein the forward primer, the reverse primer, or both primers, are phosphorylated on the 5' end; (b) performing a chain termination reaction in the presence of said forward and reverse amplification primers with a sequencing primer to generate polynucleotide fragments of at least one nucleic acid, wherein said sequencing primer is not phosphorylated on the 5' end; (c) after the chain termination reaction, enzymatically degrading chain termination extension products incorporating a phosphorylated primer using a nuclease having specificity for a 5'-phosphorylated substrate; and (d) determining the polynucleotide sequence of the at least one nucleic acid.

The methods provided herein generally find use in sequencing reactions in which the amplification step, e.g. PCR, is performed prior to the chain termination reaction, as well as in sequencing reactions wherein the amplification and chain termination reactions occur simultaneously, for example in an AmpliSeq protocol. Alternatively, the methods provided herein are also compatible with single base extension reactions. For example, methods employed to determine the identity of one or more single bases at one or more predefined sites, e.g. SNP genotyping, single base extension (SBE) sequencing, multiplex SBE, iPLEX sequencing, and the like.

In one embodiment of the SeqSharp method, both the forward and reverse amplification primers are tagged by 5'phosphorylation. Following amplification, a chain termination reaction is performed with an unphosphorylated primer. After the chain termination reaction, Lambda Exonuclease, an enzyme that degrades a 5'-OH phosphorylated strand of a double stranded DNA with high processivity (Mitsis and Kwagh, Nucleic Acids Res., 27:3057-3063 (1999)), is used to specifically digest the chain termination extension products originating from the phosphorylated primers carried over from the amplification step (FIG. 1B).

In related aspects, the invention provides methods for reducing the sequencing background generated during combined single-step amplification and chain-termination reactions (Murphy et al., Clin. Chem., 51:35-39 (2005)). In one embodiment of the present invention, two primers in unequal concentrations, for example at a 5:1 or 10:1 ratio, are added to a reaction mixture, such as Big-Dye reagent, competent for simultaneous amplification and chain termination of a target nucleic acid sequence. During the initial PCR cycles, amplification of the template is favored because the concentration of chain terminators is not sufficient enough to cause appreciable termination in the presence of added extra dNTPs. However, as amplification uses up the nucleotides, chain termination dominates over amplification in later cycles. This process leads to a dominance of fluorescence signals in the electropherogram by the primer that was present in higher concentration. However, this dominance is not complete and results, in many cases, in a significant degree of background fluorescent signal generated from chain termination products originating from the primer that was in lower concentration.

Figure 3:
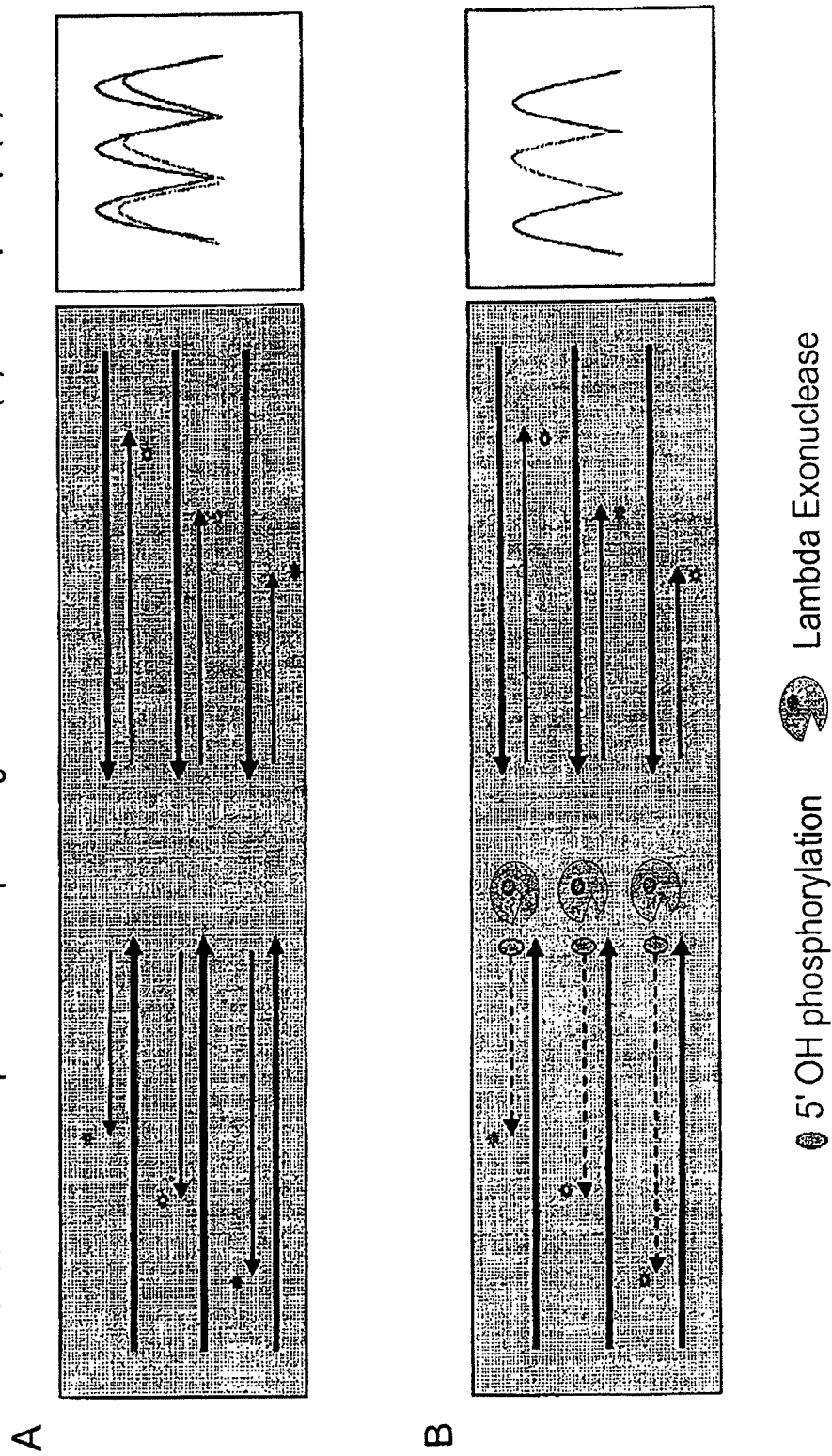
FIG. 3 A schematic diagram showing SeqSharp improves sequence quality by specifically removing tagged extension products from the minor primer in a combined amplification/chain termination protocol. Panel A shows that the presence of extension products originating from the minor primer results in multiple peaks at each base positions. Panel B shows, by specifically removing tagged (5'OH phosphorylated) chain termination product from the minor primer, SeqSharp improves the sequence data.

The AmpliSeq method, which utilizes the combined amplification and chain termination reaction protocol, can be used to determine the sequence of the repeated DNA sequence element within the *Staphylococcus aureus* protein A (spa) gene. Since this sequence information is used to distinguish *Staphylococcus aureus* strains isolated during hospital outbreaks, it is very important to have high quality of sequence information for spa repeats. A single nucleotide difference can potentially change the final conclusion and misdirect an epidemiological investigation. Although the AmpliSeq method seemed to yield good quality sequence for some *S. aureus* strains, it fails for many other strains under identical conditions. It is possible that this method is too sensitive to the concentration of starting template or other factors such as presence of PCR inhibitors that can otherwise affect a PCR reaction. Since no intermediate step for removal of unused primers can be used in a one-step combined amplification/sequencing protocol, a post-chain termination reaction step that specifically removes noise produced by the opposite strand significantly improves the outcome (FIG. 3).

In another embodiment of the present invention, two primers in approximately equal concentrations (i.e. equimolar) are added to a reaction mixture, such as Big-Dye reagent, competent for simultaneous amplification and chain termination of a target nucleic acid sequence. In another embodiment, an extra concentration of dNTPs may be added to the reaction mixture. In some embodiments, an extra concentration of dGTP may be replaced with a mixture of dITP and dGTP in order to help with uniform mobility during capillary electrophoresis. In some embodiments, the ratio of dITP to dGTP in the reaction mix may be from about 10 to 1 to about 2 to 1. In certain embodiments, the ratio of dITP to dGTP may be about 10 to 1, or about 9 to 1, or about 8 to 1, or about 7 to 1, or about 6 to 1, or about 5 to 1, or about 4 to 1, or about 3 to 1, or about 2 to 1, or about 1 to 1. In a particular embodiment, the ratio of dITP to dGTP in the reaction mix is about 4 to 1.

In another embodiment of the present invention the SeqSharp protocol is used in conjunction with a combined amplification/chain termination reaction protocol by using a 5'OH-phosphorylated version of the primer that is present at the lower concentration (minor primer). In one embodiment, a post-chain termination reaction treatment with Lambda Exonuclease improves the sequence quality by specifically cleaving the extension products originating from the minor primer (FIG. 3A vs 3B).

One embodiment of the present invention provides a method for reducing the background signal generated during a nucleic acid sequencing reaction by first amplifying a nucleic acid by a polymerase chain reaction (PCR) with a forward and a reverse primer, wherein the forward or the reverse primer is phosphorylated on the 5' end, performing a chain termination reaction in the presence of said forward and reverse PCR primers with a unphosphorylated sequencing primer to generate polynucleotide fragments of at least one targeted amino acid sequence, then enzymatically degrading chain termination extension products incorporating a phosphorylated primer using a nuclease having specificity for a 5'-phosphorylated substrate, and then determining the polynucleotide sequence of the at least one targeted amino acid sequence.

In one embodiment, both of the forward and reverse primers used for amplification are phosphorylated on the 5' end. In another embodiment, only one of the forward and reverse primers are phosphorylated. In yet another embodiment, the forward or the reverse amplification primer is the same as the sequencing primer. In some embodiments, the amplification and chain termination reactions are performed in a single step.

In some embodiments, the amplification and sequencing reactions of the invention are performed simultaneously and one of the forward or the reverse amplification primer also serves as the sequencing primer.

In another embodiment, the amplification and chain termination reactions are performed in a single step. In one embodiment, the forward and reverse primers used in the amplification step are present at unequal concentrations. In another embodiment, the forward and reverse primers used in the amplification step are present at approximately equal concentrations. Ratios of forward to reverse primers, or alternatively reverse to forward primers, for use in single step amplification/sequencing protocols are well known in the art. These ratios can be from about 500 to 1 to about 1 to 1, preferably from about 100 to 1 to about one to one, more preferably from about 30 to 1 to about 1 to 1, and most preferably from about 10 to 1 to about 1 to 1. In some embodiments, the ratio of the forward to reverse primer can be from about 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 750, or 1000 to about 1.

Thus in some embodiments, the methods of the invention involve a forward amplification primer and a reverse amplification primer, one of which is phosphorylated on the 5' end, and the other, which serves as the sequencing primer, is unphosphorylated. In some of these embodiments, the amplification primer that serves as the sequencing primer ("the sequencing primer") is present in excess of the amplification primer that does not serve as the sequencing primer ("the amplification primer"). In yet other embodiments, the sequencing primer may comprise a third primer and both the forward and the reverse primer are phosphorylated on the 5' end.

In a particular embodiment of the methods provided herein, wherein the amplification and chain termination reactions occur simultaneously, the amplification and chain termination primers may be present at or near equimolar concentrations. For example, in certain embodiments the molar ratio of amplification primers to chain termination (i.e. sequencing) primers may be about 2 to 1, or about 3 to 2, or about 5 to 4, or about 1 to 1, or about 4 to 5, or about 2 to 3, or about 1 to 2. In some embodiments, the "sequencing primer" may thus comprise the forward or reverse primer and the "amplification primer" may comprise the other.

Surprisingly, it was found that in single step amplification/sequencing reactions that using an equimolar ratio of forward primer to reverse primer work as well, and in some cases better, than using a nonequimolar ratio. Thus, in one embodiment, methods are provided for single step amplification and sequencing reactions that use equimolar amounts of forward and reverse primer, wherein one of the primers is 5'-phosphorylated and the other is not (i.e., the primer that is also used for sequencing).

Nucleases well suited for degradation of unwanted chain termination reaction products are well known in the art and include, but are not limited to, lambda exonuclease. In one preferred embodiment, the nuclease is lambda exonuclease. In one embodiment, the nuclease is recombinantly produced. In another embodiment, the recombinantly produced nuclease may further comprise a fusion protein or a tag used to facilitate purification. Many polypeptide tags particularly well suited for facilitating purification are well in the art and include, but are not limited to, polyhistidine (His) tags, GST-tags, strep-tags, calmodulin-binding peptide tags, chitin-binding protein tags, maltose-binding protein (MBP) tags, intein based tags, FLAG tags, myc tags, HA tags, and many others well known in the art. In another embodiment, nuclease may comprise a functional fragment of a wild-type or engineered nuclease.

The template DNA used in the present invention can be a plasmid, a bacmid, a cosmid, a recombinant virus, an artificial chromosome, isolated total genomic DNA, a recombinant plasmid, cDNA, a synthetic DNA, or any other suitable nucleic acid template for amplification well known in the art. In a preferred embodiment, the template nucleic acid is isolated from an infectious agent. A large number of infectious agents are well known in the art and include, but are not limited to, RNA viruses, DNA viruses, bacteria, fungi, protozoa, and multicellular parasites. In another embodiment, the infectious agent is a strain of *Staphylococcus*. In yet another embodiment, the infectious agent can be directly detected from a clinical specimen without prior amplification. In one embodiment of the present invention, the template DNA need not be preheated before being used in an amplification reaction.

In certain embodiments, the methods of the invention may be used to identify or to determine the strain of an organism. In a particular embodiment, the methods of the invention are useful for determining a species of bacteria in a biological or clinical sample. In one embodiment, the method may be used to determine the 16S gene sequence, or a portion thereof, sufficient to determine the identity of a species. In another specific embodiment, the methods of the invention may be useful for determining the repeat sequence with the *Staphylococcus* protein A (spa) gene. This method may be particularly useful for determining the degree of relatedness between a spa gene from a *Staphylococcus* found in a biological or clinical sample, and spa gene in a MRSA strain. Or for determining the degree of relatedness between spa genes in related MRSA strains. In yet other embodiments, the methods provided herein may find use in determining the sequence of a 28S or ITS (internal transcribed spacer) loci within a fungal ribosomal gene sequence. Non-limiting examples of forward and reverse primers that may be used for sequencing a fungal ITS or 28S loci include:

```
Primer sequences for ITS locus
                                     (SEQ ID NO: 12)
    ITS1    5'-TCC GTA GGT GAA CCT GCG G-3'

(SEQ ID NO: 13)
    ITS2    5'-GCT GCG TTC TTC ATC GAT GC-3'

Primer sequences for 28S locus
                                     (SEQ ID NO: 14)
    NL1     5'-GCA TAT CAA TAA GCG GAG GAA AAG-3'

(SEQ ID NO: 15)
    NL4     5'-GGT CCG TGT TTC AAG ACG G-3'
```

In one embodiment, the present invention provides kits for the production of nucleic acid sequencing results with reduced background generated by unwanted extension products, containing dNTPs, ddNTPs, a polymerase, a concentrated reaction buffer, and a nuclease. In some embodiments the kits further contain primers for both amplification and chain termination reactions. In another embodiment, the kit contains more than one forward amplification, reverse amplification, or chain termination reaction primer. In a preferred embodiment, the polymerase provided is suitable for both amplification and chain termination reactions. In another preferred embodiment, the nuclease has specificity or increased substrate affinity for a modified nucleic acid substrate. In a particularly preferred embodiment, the nuclease has specificity or increased substrate affinity for 5'-OH phosphorylated DNA. In another preferred embodiment, the concentrated buffer provided in the kit is suitable for amplification, chain termination, and nuclease reactions.

In one embodiment, kits are provided for determining the presence, identity, or strain of a bacterium in a biological or clinical sample. In another embodiment, the present invention provides kits for determining the presence, identity, or strain of a multidrug-resistant *Staphylococcus aureus* (MRSA) or oxacillin-resistant *Staphylococcus aureus* (ORSA) in a biological or clinical sample. In yet another embodiment, kits are provided for determining the presence, identity, or strain of a fungus in a biological or clinical sample.

Suitable buffers for amplification, chain termination, and nuclease reactions are well known in the art and can be found, for example, in various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document.

Suitable polymerases for amplification and chain termination reactions are well known in the art and include, but are not limited to, Taq, Vent, Deep Vent, pfu, pfu turbo, Herculase, Herculase II, Replinase, DNA Pol I, the Klenow fragment of DNA Pol I, and many others well known in the art.

In another embodiment, the invention provides methods of reducing the background signal of a sequencing reaction following amplification of at least one target sequence by a suitable amplification methods. Many suitable amplification methods are well known in the art and include, but are not limited to PCR, colony PCR, helicase-dependent amplification, Hot-start PCR, inverse PCR, ligation-mediated PCR, methylation-specific PCR, mulitiplex PCR, nested PCR, overlap-extension PCR, RT-PCR, Tail PCR, touchdown PCR, PAN-AC, and many other suitable amplification methods well known in the art.

In one aspect of the invention, methods are provided for reducing the background signal of a single base extension reaction. In a particular embodiment, the method comprises the steps of (a) amplifying a nucleic acid by an amplification reaction, for example PCR, with a forward and a reverse primer, wherein the forward primer, the reverse primer, or both are phosphorylated on the 5' end; (b) performing a single base extension reaction in the presence of said forward and reverse amplification primers with an extension primer to generate single base extension products, wherein said extension primer is not phosphorylated on the 5' end; (c) after the single base extension reaction, enzymatically degrading extension products incorporating a phosphorylated primer using a nuclease having specificity for a 5'-phosphorylated substrate; and (d) determining the identity of the incorporated nucleotide in the extension reaction product.

Single base extension (SBE) reaction methods for determining the identity of single nucleotides at a plurality of genomic loci in a single reaction, i.e. multiplex reaction, are well known in the art (see, for example, U.S. Pat. Nos. 5,888, 819; 6,004,744; 7,074,597; Kim et al., Nucleic Acids Res. 2002 Aug. 15; 30(16):e85; Yang et al., Anal Biochem. 2003 Mar. 1; 314(1):54-62; and Ross et al., Nat Biotechnol. 1998 December; 16(13):1347-51). However, the total number of loci which can be genotyped in a single reaction are limited by background noise generated from single base extension products incorporating primers carried over from the amplification step of the reaction. This problem is especially prevalent in large multiplex reactions, for example 15-25 loci per reaction, because two amplification primers are used for every loci that is to be genotyped. In certain schemes, the length, and therefore the relative molecular weight, of all of the amplification primers is set at an outer limit, for example 30 to 35 bp, and the sequencing primers are then varied from roughly 12 to 30 bp in length. As such, the identity of the loci can be uniquely determined by the molecular weight of the SBE reaction product, for example via MALDI-TOF MS, i.e. each loci has a different molecular weight dependent upon the length of the primer used for the particular loci. However, due to the large number of 30-35 bp amplification primers used, this region of the MS spectrum cannot be utilized to further extend the total number of loci genotyped in a single multiplex reaction.

Advantageously, the methods of the present invention allow for a greater number of SBE genotyping reactions in a single multiplex reaction. This is accomplished by using 5'-phosphorylated amplification primers and unphosphorylated sequencing primers. The sequential amplification and chain termination (SBE) reactions are performed and then the extension products incorporating 5'-phosphorylated amplification primers are degraded using a nuclease having specificity for a 5'-phosphorylated substrate, for example, lambda exonuclease.

In certain embodiments, a method of genotyping a plurality of SNPs in a biological sample comprises the steps of: (a) amplifying a plurality of genomic loci by an amplification reaction with a plurality of forward and reverse amplification primer pairs, wherein at least one of the forward or the reverse primers of each primer pair is phosphorylated on the 5' end; (b) after the amplification reaction, removing residual dNTPs from the reaction mixture; (c) performing a single base extension reaction in the presence of said amplification primer pairs with a plurality of sequencing primers to generate single base primer extension products, wherein said sequencing primer is not phosphorylated on the 5' end; (d) after the single base extension reaction, enzymatically degrading single base extension reaction products incorporating a phosphorylated primer using a nuclease having specificity for a 5'-phosphorylated substrate; and (e) determining the identity of the nucleotide present at each genomic loci.

In certain embodiments, wherein the amplification primers and the sequencing primers are not the same, both the forward and reverse amplification primers in each primer pair are phosphorylated on the 5' end. In other embodiments, wherein a forward or reverse amplification primer is the same as a sequencing primer, the opposite primer of the pair is phosphorylated. For example, in certain embodiments a forward amplification primer for a particular loci will also serve as a sequencing primer for a single base extension reaction. In this case, the forward amplification primer is not phosphorylated, while the reverse amplification primer is.

In certain embodiments, the methods provided herein are useful for determining the identity of a single nucleotide at least about 5 genomic loci. In other embodiments, the methods are useful for genotyping at least about 6, 7, 8, 9, 10, 11, 12, 13, 14, 15, 16, 17, 18, 19, 20, 21, 22, 23, 24, 25, 26, 27, 28, 29, 30, 35, 40, or more loci.

In certain embodiments of the methods provided herein, residual dNTPs may be removed by treating the sample with an alkaline phosphatase, for example a shrimp alkaline phosphatase (SAP). In other embodiments, the dNTPs may be removed by separating them from the amplification reaction products, for example via a size exclusion or affinity column.

The identity of the nucleotides incorporated into the single base extension reactions may be determined, for example, by chromatography, by separation via electrophoresis, or by mass spectrometry. In a particular embodiment, the identity of the nucleotide is determined by matrix-assisted laser desorption ionization time of flight mass spectrometry (MALDI-TOF MS). In some embodiments, the chain terminator nucleotides used in the chain termination reactions of the invention may be labeled, for example, by a fluorescent label, a mass label, a radioactive label, an enzymatic label, and the like.

In a related aspect, the present invention provides methods of diagnosing or providing a prognosis for a disease associated with a genetic component in a subject in need thereof. In certain embodiments, the methods comprise determining the sequence of a polynucleotide or the identity a SNP from a biological sample from the individual, using a method provided herein. In certain embodiments, the methods of the invention allow for the diagnosis, prognosis, or screening of a plurality of SNPs in a biological sample from a subject.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, molecular biology, organic chemistry, nucleic acid chemistry, PCR, and nucleic acid sequencing described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y.), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "allele" has the meaning conventionally associated with this term in genetics and generally refers to any of a number of alternative forms of a gene or segment of the chromosome.

"Reducing background signal" refers to any reduction in signal generated during DNA sequencing due to the carry over of primers from the amplification step as compared to a control reaction that does not use the methods of the present invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or "detectable label" is a composition detectable by spectroscopic, photochemical, biochemical, immunochemical, or chemical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available.

An "amplification reaction" refers to any chemical reaction, including an enzymatic reaction, which results in increased copies of a template nucleic acid sequence. Amplification reactions include polymerase chain reaction (PCR) and ligase chain reaction (LCR) (see U.S. Pat. Nos. 4,683,195 and 4,683,202; *PCR Protocols: A Guide to Methods and Applications* (Innis et al., eds, 1990)), strand displacement amplification (SDA) (Walker, et al. *Nucleic Acids Res.* 20(7): 1691 (1992); Walker *PCR Methods Appl* 3(1):1 (1993)), transcription-mediated amplification (Phyffer, et al., *J. Clin.*

*Microbiol.* 34:834 (1996); Vuorinen, et al., *J. Clin. Microbiol.* 33:1856 (1995)), nucleic acid sequence-based amplification (NASBA) (Compton, *Nature* 350(6313):91 (1991), rolling circle amplification (RCA) (Lisby, *Mol. Biotechnol.* 12(1):75 (1999)); Hatch et al., *Genet. Anal.* 15(2):35 (1999)), branched DNA signal amplification (bDNA) (see, e.g., Iqbal et al., *Mol. Cell Probes* 13(4):315 (1999)), linear amplification, and the like.

"Amplifying" refers to submitting a solution to conditions sufficient to allow for amplification of a polynucleotide if all of the components of the reaction are intact. Components of an amplification reaction include, e.g., primers, a polynucleotide template, polymerase, nucleotides, and the like. Thus, an amplifying step can occur without producing a product if, for example, primers are degraded.

"Amplification reagents" refer to reagents used in an amplification reaction. These reagents can include, e.g., oligonucleotide primers; borate, phosphate, carbonate, barbital, Tris, etc. based buffers (see, U.S. Pat. No. 5,508,178); salts such as potassium or sodium chloride; magnesium; deoxynucleotide triphosphates (dNTPs); a nucleic acid polymerase such as Taq DNA polymerase; as well as DMSO; and stabilizing agents such as gelatin, bovine serum albumin, and non-ionic detergents (e.g. Tween-20).

As used herein, a "chain termination reaction" refers to a nucleotide extension reaction, in which a primer is extended by at least one nucleotide and terminates with the incorporation of a terminator nucleotide, for example a dideoxynucleotide. As such, as used herein, chain termination reactions include both cycle sequencing reactions (e.g. Sanger sequencing reactions) and single base extension reactions (e.g. SBE or iPLEX reactions).

The term "primer" refers to a nucleic acid sequence that primes the synthesis of a polynucleotide in an amplification reaction. Typically a primer comprises fewer than about 100 nucleotides and preferably comprises fewer than about 30 nucleotides. Exemplary primers range from about 5 to about 30 nucleotides. Preferred primers can be, for example, about 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 nucleotides. The "integrity" of a primer refers to the ability of the primer to prime an amplification reaction. For example, the integrity of a primer is typically no longer intact after degradation of the primer sequences such as by endonuclease cleavage.

A "target" or "target sequence" refers to a single or double stranded polynucleotide sequence sought to be amplified in an amplification reaction and/or sequenced, for example, after a chain termination reaction. Two target sequences are different if they comprise non-identical polynucleotide sequences.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 20 amino acids or nucleotides in length, or more preferably over a region that is 20-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used. Other algorithms well known in the art can additionally be used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by manual alignment and visual inspection (see, e.g., Current Protocols in Molecular Biology (Ausubel et al., eds. 1995 supplement)), or by structural superposition and manual inspection.

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

EXAMPLES

Example 1

We used SeqSharp to sequence the first 500 base pairs of bacterial 16S rRNA gene, a common target for amplification and cycle sequencing for identification of bacteria at the species level. To do so, bacterial genomic DNA was isolated by Ultraclean DNA extraction kit (MoBio Lab Inc., Carlsbad, Calif.) following the procedure recommended by the manufacturer. All primers, phosphorylated and unphosphorylated were purchased from Invitrogen (Carlsbad, Calif.).

SeqSharp for sequencing PCR amplified DNA fragment: PCR for amplifying the first 500 bps of the 16S bacterial ribosomal gene was performed in a final volume of 50 μl with 1× AmpliTaq Buffer, 3 mM MgCl$_2$, 200 μM dNTPs, 1 μM primers (5'OH phosphorylated 16SF and 16SR (SEQ ID NOS:21 and 22)), 1-10 ng of bacterial genomic DNA and 1.25 units of AmpliTaq (Applied Biosystems, Foster City, CA). The sequence of the primers, 16SF and 16SR were 5'-AGAGTTTGATCCTGGCTCAG-3' (SEQ ID NO:7) and 5'-TTACCGCGGCTGCTGGCA-3' (SEQ ID NO:8), respectively.

The PCR condition for the amplification was initial denaturation at 95° C. for 10 mins, 30 cycles of 95° C. for 30 sec, 68° C. for 30 sec, 72° C. for 45 sec and a final extension at 72° C. for 10 mins. Amplification of the 16S gene fragment was confirmed by agarose gel electrophoresis and 2 µl of the PCR product was used in a 10 µl chain termination reaction using ABI Big-dye (v 3.1) reagent (Applied Biosystems, Foster City, Calif.). Final concentration of primer (unphosphorylated 16SF or 16SR) in the sequencing reaction was 1 µM.

The conditions for the chain termination reaction were 25 cycles of 96° C. at 10 sec, 50° C. at 5 sec and 60° C. at 4 mins. After the chain termination reaction was completed, we treated the products with 2.5 units of Lambda Exonuclease (New England Biolabs, Ipswich, Mass.) at 37° C. for 30 mins. Big-dye reaction products were purified using the X-terminator kit (Applied Biosystems, Foster City, Calif.).

Traditional sequencing of the PCR amplified DNA fragment (16S gene) was done following the identical procedure as described above, except that unphosphorylated primers (SEQ ID NOS:7 and 8) were used and the sequencing reaction products were not subjected to Lambda Exonuclease digestion. Nucleotide sequences for both reactions were determined by using an Applied Biosystems 3130 Genetic Analyzer.

Figure 2:
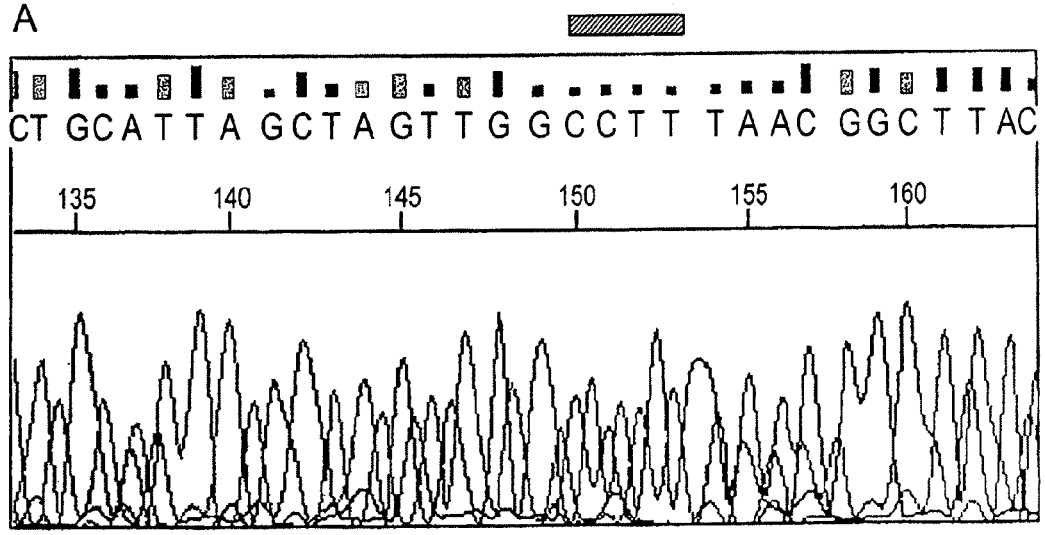
FIG. 2 Improvement of sequence quality by SeqSharp. Panel A shows the 16S sequence data obtained when amplification primers were not removed before or after the Big-dye sequencing reaction. A partial sequence as determined with the traditional PCR method is shown above the electropherogram (SEQ ID NO:1). Panel B shows the improved sequence data when SeqSharp method was incorporated. Solid black bar highlights a stretch of 4-5 bases where base-calls were affected within the section of electropherograms shown. A partial sequence as determined with the SeqSharp method is shown above the electropherogram (SEQ ID NO:2).
Figure 2:
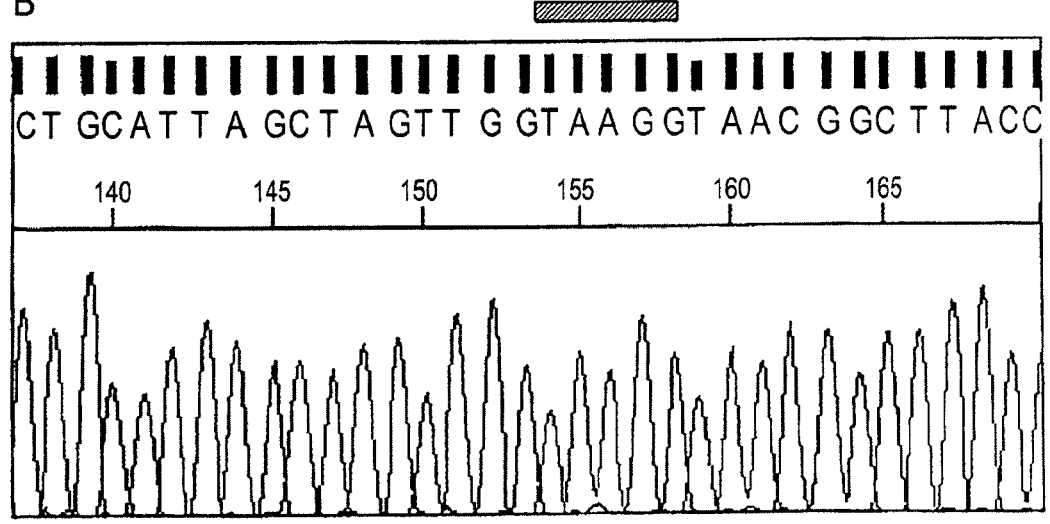

FIG. 2 shows a section of the electropherogram of the 16S sequence obtained using a conventional amplification and sequencing (Panel A) and with SeqSharp (Panel B). The quality of electropherogram was markedly improved by SeqSharp method and multiple bases were not called correctly by the base calling software without SeqSharp (flagged by solid bars). This result indicates that a post-sequencing treatment with Lambda Exonuclease is sufficient to remove background signals due to the extension of the oppositely oriented phosphorylated amplification primer. These observations were also supported by the quality scores determined by the Applied Biosystems' KB basecaller software. Average contiguous read length (CRL) and the number of bases with predicted <1% error in base calling (QV20+) were 430 and 426 respectively for sequences obtained by SeqSharp, compared to 157 and 192 for conventional amplification and sequencing.

Example 2

The SeqSharp method was used in a combined amplification/chain termination reaction in order to determine the sequence of the repeated DNA sequence element within the *Staphylococcus aureus* protein A (spa) gene. Since this sequence information is used to distinguish *Staphylococcus aureus* strains isolated during hospital outbreaks, it is very important to have high quality of sequence information for spa repeats. A single nucleotide difference can potentially change the final conclusion and misdirect an epidemiological investigation.

SeqSharp for combined amplification/sequencing: For combined amplification/chain termination reaction of the spa repeats, a 10 l reaction was set up with Applied Biosystems' Big-dye reagent (v 3.1). The amplification/sequencing reaction for the forward strand contained 1 µM primer 1095F (5'-AGACGATCCTTCGGTGAGC-3') (SEQ ID NO:16), 0.1 M 5'—OH phosphorylated primer 1517R (5'- GCTTTTG-CAATGTCATTTACTG-3') (SEQ ID NO:17). Amplification/sequencing of the spa reverse strand was accomplished by using 1 µM 1517R (SEQ ID NO:18) and 0.1 µM 5' OH phosphorylated 1095F (SEQ ID NO:19). Extra dNTPs to a final concentration of 125 µM was added to favor amplification over chain termination during initial temperature cycles. *Staphylococcus aureus* genomic DNA (1 to 10 ng) was added to the reaction mix after the DNA was incubated for 15 min at a 95° C. heat-block.

The amplification/sequencing was performed on ABI Geneamp 9700 with the following cycling parameters; initial denaturation at 94° C. for 30 sec, followed by 40 cycles consisting of 95° C. for 5 sec, 50° C. for 20 sec and 60° C. for 4 min, followed by a hold at 4° C. The single step amplification/sequencing products were treated with 2.5 units of Lambda Exonuclease for 30 min at 37° C. and purified with X-terminator kit (Applied Biosystems, Carlsbad, Calif.).

Traditional sequencing of the one-step combined amplification and sequencing (spa repeats) was also performed following the identical procedure as described above, except that unphosphorylated primers were used and the chain termination reaction products were not subjected to Lambda Exonuclease digestion. Nucleotide sequences for both reactions were determined by using an Applied Biosystems 3130 Genetic Analyzer.

Figure 4:
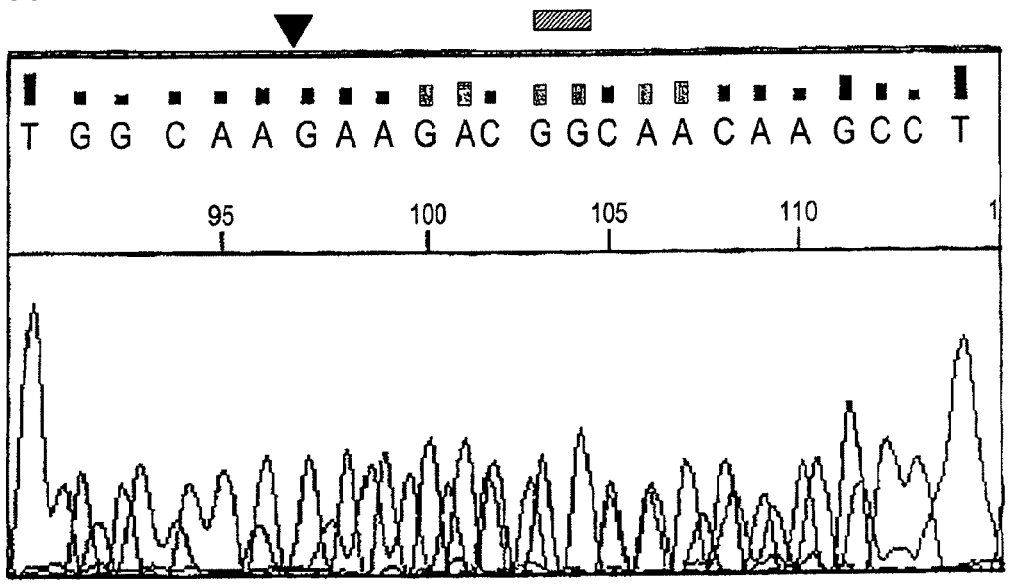
FIG. 4 Improvement of combined amplification/chain termination reaction sequence data by specific removal of chain termination product originating from the minor primer. Panel A shows a section of results obtained by traditional methods for *Staphylococcus aureus* protein A (spa) repeat sequences with multiple peaks at many base positions. A partial sequence as determined with the traditional method is shown above the electropherogram (SEQ ID NO:3) Panel B shows results of AmpliSeq for the same section improved by SeqSharp. Solid black bar and an inverted triangle highlight positions where base-calls were different within the section of electropherograms shown. A partial sequence as determined with the SeqSharp method is shown above the electropherogram (SEQ ID NO:4).
Figure 4:
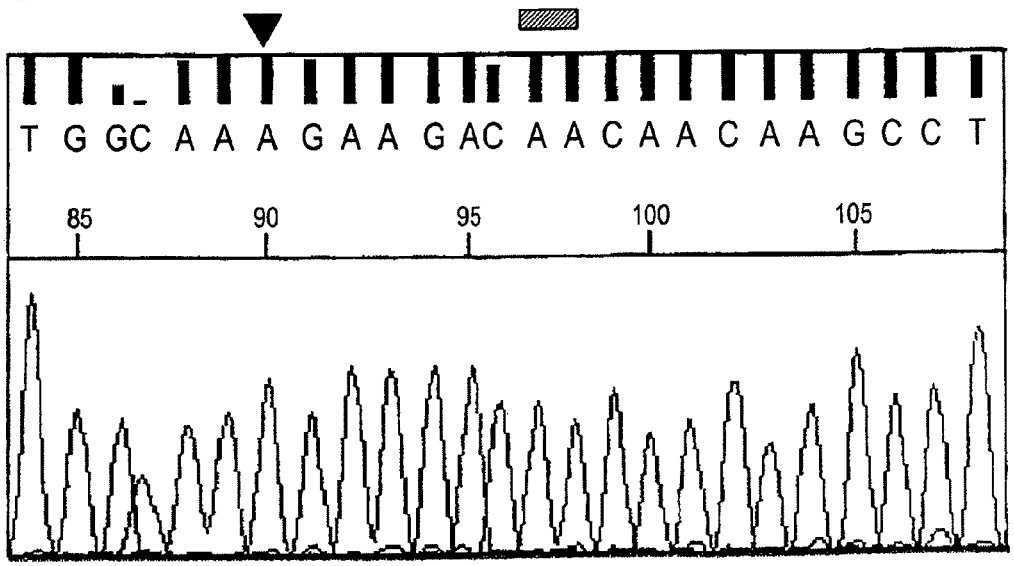

When the spa repeat element was sequenced by a combined amplification/chain termination protocol incorporating SeqSharp by including a phosphorylated minor primer and Lambda Exonuclease treatment at the end, the quality of the DNA sequence obtained was markedly improved (FIG. 4A vs 4B). Multiple basecalls were wrong with AmpliSeq alone, including one that suggested deletion of a base. The observed improvement in sequence quality by SeqSharp was also supported by the quality scores determined by Applied Biosystems' KB basecaller. Average contiguous read length (CRL) and number of bases that were called with a predicted error rate of <1% (QV20+) were 303 and 292 respectively for AmpliSeq with SeqSharp, compared to 131 and 53 when the only AmpliSeq procedure was used. These results indicate that the SeqSharp can be valuable for improving the quality of data obtained by a one step combined amplification/sequencing protocol.

Example 3

The SeqSharp combined amplification/sequencing method described in Example 2 was modified in several respects and then tested to determine whether the modified method would still yield comparable quality sequencing data in sequencing the first 500 base pairs of bacterial 16S rRNA gene, a common target for amplification and cycle sequencing for identification of bacteria at the species level. One modification was the use of phosphorylated and unphosphorylated primers in equimolar quantity rather than at an unequal ratio. Another modification was the replacement of dGTP with a mixture of dITP and dGTP at a 4:1 ratio. Additionally, the bacterial genomic DNA was not preheated before being added to the amplification/sequencing reaction mix.

SeqSharp for combined amplification/sequencing: For combined amplification/chain termination reaction of the bacterial 16S rRNA gene, a 10 µl reaction was set up with Applied Biosystems' Big-dye reagent (v 3.1). The amplification/sequencing reaction for the forward strand contained equal concentrations of unphosphorylated 16SF (SEQ ID NO:7) primer and phosphorylated 16SR-3 (SEQ ID NO:21) primer. The amplification/sequencing reaction for the reverse strand contained equal concentrations of unphosphorylated 16SR-3 (SEQ ID NO:9) primer and phosphorylated 16SF (SEQ ID NO:20) primer. Extra dNTPs to a final concentration of 125 µM was added to favor amplification over chain termination during initial temperature cycles. Bacterial genomic DNA (1 to 10 ng) was added to the reaction mix. The sequence of the primers, 16SF and 16SR-3, were 5'-AGAGTTTGATCCTGGCTCAG-3' (SEQ ID NO:7) and 5'-TTACCGCGGCTGCTG-3' (SEQ ID NO:9), respectively.

The amplification/sequencing was performed on ABI Geneamp 9700 with the following cycling parameters; initial denaturation at 94° C. for 30 sec, followed by 40 cycles consisting of 95° C. for 5 sec, 50° C. for 20 sec and 60° C. for 4 min, followed by a hold at 4° C. The single step amplification/sequencing products were treated with 2.5 units of Lambda Exonuclease for 30 min at 37° C. and purified with X-terminator kit (Applied Biosystems, Carlsbad, Calif.).

Figure 5:
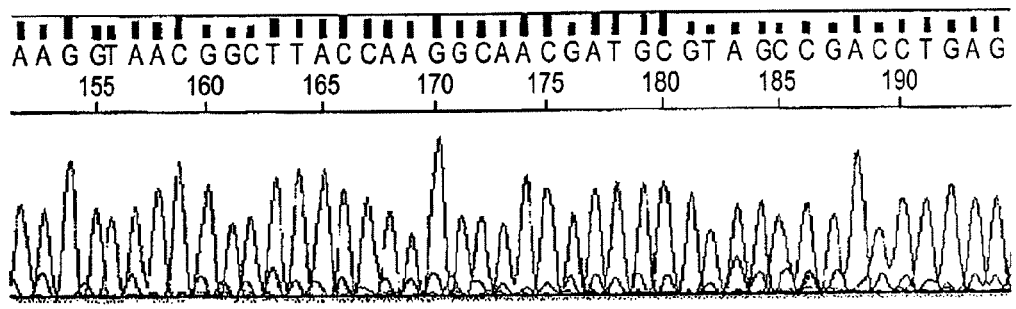
FIG. 5 Sequence data from SeqSharp can be obtained using an equimolar ratio of amplification primers. Panel A shows a section of results obtained by the SeqSharp method for the forward strand of the bacterial 16S rRNA gene. A partial sequence as determined with the SeqSharp method is shown above the electropherogram (SEQ ID NO:5). Panel B shows a section of results obtained by the SeqSharp method for the reverse strand of the bacterial 16S rRNA gene. A partial sequence as determined with the SeqSharp method is shown above the electropherogram (SEQ ID NO:6).
Figure 5:
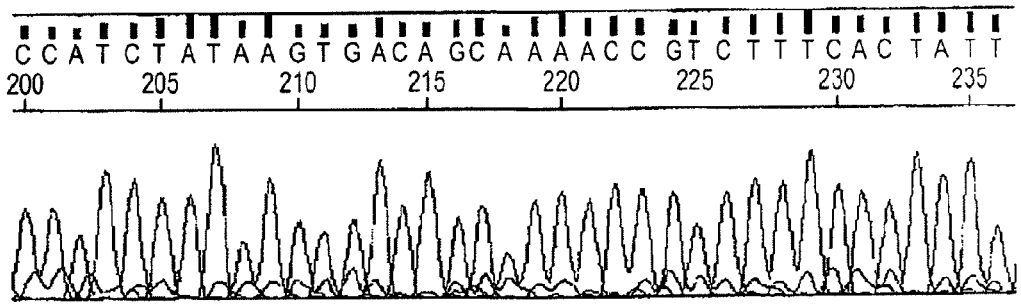
Figure 6:
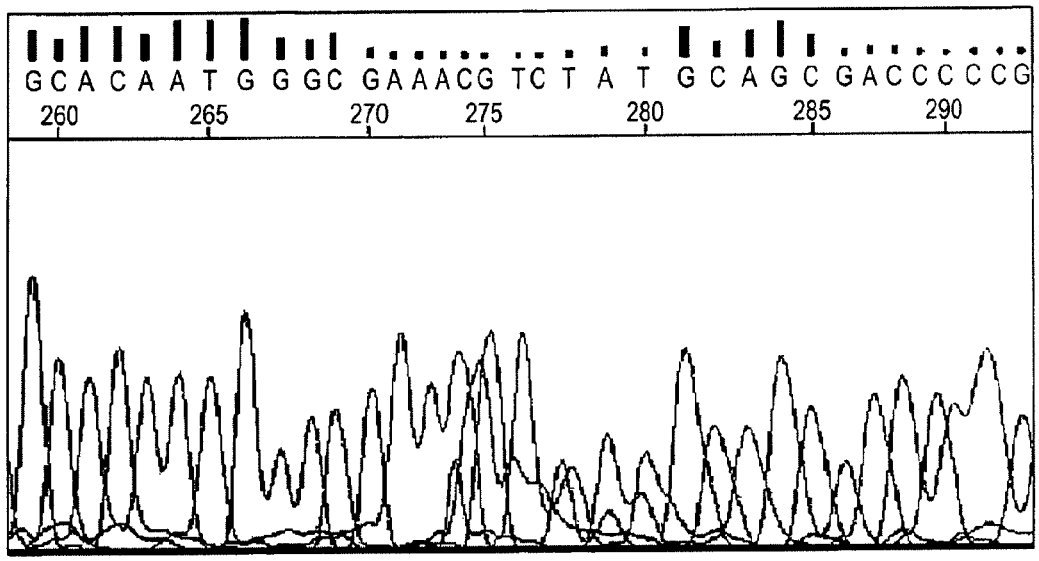
FIG. 6 Comparison of the sequencing results for a specific loci within the *Nocardia farcinica* 16S genomic sequence using reaction mixes with (B) and without (A) dITP. Panel A shows an aberrant electropherogram profile when a dNTP mix comprising dGTP, dATP, dCTP and dTTP was used (SEQ ID NO:10). Panel B shows an improved electropherogram when dGTP was replaced by a 4:1 mixture of dITP: dGTP (SEQ ID NO:11). Primers and SeqSharp method were otherwise utilized as described herein.
Figure 6:
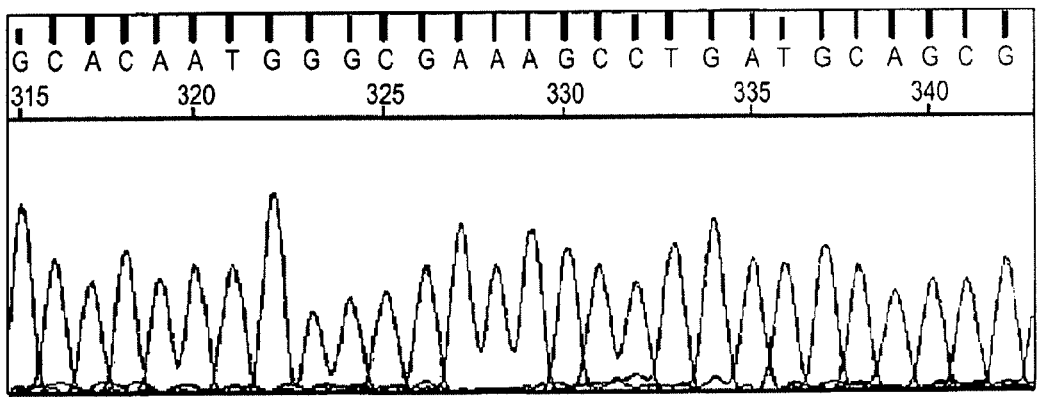

The quality of sequence obtained from this modified method for the bacterial 16S rRNA forward and reverse strands (FIGS. 5A and 5B) was consistent with the quality of sequence obtained by the SeqSharp combined amplification/sequencing method of Example 2 (FIG. 4B). These results indicate that an equimolar ratio of primers can be used in the SeqSharp one step combined amplification/sequencing protocol without sacrificing the improvement in quality of data.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing the background signal generated during a nucleic acid sequencing reaction, the method comprising the steps of:
   (a) amplifying a nucleic acid by an amplification reaction with a forward and a reverse primer, wherein the forward or the reverse primer is phosphorylated on the 5' end;
   (b) performing a chain termination reaction in the presence of said forward and reverse amplification primers with a sequencing primer to generate primer extension products incorporating at least one additional nucleotide, wherein said sequencing primer is not phosphorylated on the 5' end;
   (c) after the chain termination reaction, enzymatically degrading chain termination extension products having said phosphorylated primer incorporated thereto using a nuclease having specificity for a 5'-phosphorylated substrate; and
   (d) determining the polynucleotide sequence of the amplified nucleic acid.

2. The method of claim 1, wherein the amplification reaction is a polymerase chain reaction (PCR).

3. The method of claim 1, wherein said amplification reaction occurs prior to said chain termination reaction.

4. The method of claim 1, wherein said amplification reaction occurs simultaneous to said chain termination reaction.

5. The method of claim 1, wherein said amplification reaction utilizes a 5'-phosphorylated forward primer.

6. The method of claim 1, wherein said amplification reaction utilizes a 5'-phosphorylated reverse primer.

7. The method of claim 1, wherein said amplification reaction utilizes both a 5'-phosphorylated forward primer and a 5'-phosphorylated reverse primer.

8. The method of claim 1, wherein the chain termination reaction is a single base extension reaction.

9. The method of claim 1, wherein the method comprises the use of more than one sequencing primer.

10. The method of claim 1, wherein the ratio of the concentration of the amplification primer(s) to the concentration of the sequencing primer(s) is from about 100 to 1 to about 1 to 1.

11. The method of claim 10, wherein the said ratio is from about 30 to 1 to about 1 to 1.

12. The method of claim 10, wherein the said ratio is from about 10 to 1 to about 1 to 1.

13. The method of claim 10, wherein the sequencing primer is not used in the amplification reaction.

14. The method of claim 1, wherein the amplification primer(s) and sequencing primer(s) are present at equimolar concentrations.

15. The method of claim 1, wherein said nuclease is selected from the group consisting of lambda exonuclease, a functionally equivalent fragment thereof, and a nuclease that is functionally equivalent to lambda exonuclease.

16. The method of claim 1, wherein the chain termination reaction comprises the use of dITP.

17. The method of claim 16, wherein the chain termination reaction comprises the use of dITP and dGTP at a molar ratio of from about 10 to 1 to about 2 to 1.

18. The method of claim 17, wherein the molar ratio of dITP to dGTP is about 4 to 1.

19. The method of claim 1, wherein the nucleic acid to be amplified is not preheated prior to amplification.

20. The method claim 1, wherein the method is for determining the sequence of more than one amplified nucleic acid.

21. A method of genotyping a plurality of SNPs in a biological sample, the method comprising the steps of:
   (a) amplifying a plurality of genomic loci by an amplification reaction with a plurality of forward and reverse amplification primer pairs, wherein at least one of the forward or the reverse primers of each primer pair is phosphorylated on the 5' end;
   (b) after the amplification reaction, removing residual dNTPs from the reaction mixture;
   (c) performing a single base extension reaction in the presence of said amplification primer pairs with a plurality of sequencing primers to generate single base primer extension products, wherein said sequencing primer is not phosphorylated on the 5' end;
   (d) after the single base extension reaction, enzymatically degrading single base extension reaction products having said phosphorylated primer incorporated thereto using a nuclease having specificity for a 5'-phosphorylated substrate; and
   (e) determining the identity of the nucleotide present at each genomic loci.

22. A method of diagnosing or providing a prognosis for a disease associated with a genetic component in a subject in need thereof, the method comprising genotyping a plurality of SNPs in a biological sample from the subject with a method of claim 21.

* * * * *

```
                          SEQUENCE LISTING

<160> NUMBER OF SEQ ID NOS: 22

<210> SEQ ID NO 1
<211> LENGTH: 32
<212> TYPE: DNA
<213> ORGANISM: Artificial Sequence
<220> FEATURE:
<223> OTHER INFORMATION: synthetic bacterial 16S ribosomal rRNA gene
      partial sequence determined with traditional PCR
      method

<400> SEQUENCE: 1
ctgcattagc tagttggcct ttaacggctt ac                                  32

<210> SEQ ID NO 2
<211> LENGTH: 34
<212> TYPE: DNA
<213> ORGANISM: Artificial Sequence
<220> FEATURE:
<223> OTHER INFORMATION: synthetic bacterial 16S ribosomal rRNA gene
      partial sequence determined with SeqSharp method

<400> SEQUENCE: 2
ctgcattagc tagttggtaa ggtaacggct tacc                                34

<210> SEQ ID NO 3
<211> LENGTH: 24
<212> TYPE: DNA
<213> ORGANISM: Artificial Sequence
<220> FEATURE:
<223> OTHER INFORMATION: synthetic Staphylococcus aureus protein A (spa)
      repeat partial sequence determined with
      traditional PCR method

<400> SEQUENCE: 3
tggcaagaag acggcaacaa gcct                                           24

<210> SEQ ID NO 4
<211> LENGTH: 25
<212> TYPE: DNA
<213> ORGANISM: Artificial Sequence
<220> FEATURE:
<223> OTHER INFORMATION: synthetic Staphylococcus aureus protein A (spa)
      repeat partial sequence determined with SeqSharp
      method

<400> SEQUENCE: 4
tggcaaagaa gacaacaaca agcct                                          25

<210> SEQ ID NO 5
<211> LENGTH: 43
<212> TYPE: DNA
<213> ORGANISM: Artificial Sequence
```

```
<220> FEATURE:
<223> OTHER INFORMATION: synthetic bacterial 16S ribosomal rRNA gene
      forward strand partial sequence determined with
      SeqSharp method

<400> SEQUENCE: 5
aaggtaacgg cttaccaagg caacgatgcg tagccgacct gag                     43

<210> SEQ ID NO 6
<211> LENGTH: 37
<212> TYPE: DNA
<213> ORGANISM: Artificial Sequence
<220> FEATURE:
<223> OTHER INFORMATION: synthetic bacterial 16S ribosomal rRNA gene
      reverse strand partial sequence determined with
      SeqSharp method

<400> SEQUENCE: 6
ccatctataa gtgacagcaa aaccgtcttt cactatt                            37

<210> SEQ ID NO 7
<211> LENGTH: 20
<212> TYPE: DNA
<213> ORGANISM: Artificial Sequence
<220> FEATURE:
<223> OTHER INFORMATION: synthetic bacterial 16S ribosomal rRNA gene
      unphosphorylated primer 16SF

<400> SEQUENCE: 7
agagtttgat cctggctcag                                               20

<210> SEQ ID NO 8
<211> LENGTH: 18
<212> TYPE: DNA
<213> ORGANISM: Artificial Sequence
<220> FEATURE:
<223> OTHER INFORMATION: synthetic bacterial 16S ribosomal rRNA gene
      unphosphorylated primer 16SR

<400> SEQUENCE: 8
ttaccgcggc tgctggca                                                 18

<210> SEQ ID NO 9
<211> LENGTH: 15
<212> TYPE: DNA
<213> ORGANISM: Artificial Sequence
<220> FEATURE:
<223> OTHER INFORMATION: synthetic bacterial 16S ribosomal rRNA gene
      unphosphorylated primer 16SR-3

<400> SEQUENCE: 9
ttaccgcggc tgctg                                                    15

<210> SEQ ID NO 10
<211> LENGTH: 29
<212> TYPE: DNA
<213> ORGANISM: Artificial Sequence
<220> FEATURE:
<223> OTHER INFORMATION: synthetic Nocardia farcinica 16S genomic
      partial sequence determined without dITP in reaction mixture

<400> SEQUENCE: 10
gcacaatggg cgaaacgtct atgcagcga                                     29

<210> SEQ ID NO 11
<211> LENGTH: 28
<212> TYPE: DNA
<213> ORGANISM: Artificial Sequence
```

```
<220> FEATURE:
<223> OTHER INFORMATION: synthetic Nocardia farcinica 16S genomic
      partial sequence determined with dITP in reaction mixture

<400> SEQUENCE: 11
gcacaatggg cgaaagcctg atgcagcg                                      28

<210> SEQ ID NO 12
<211> LENGTH: 19
<212> TYPE: DNA
<213> ORGANISM: Artificial Sequence
<220> FEATURE:
<223> OTHER INFORMATION: synthetic fungal ribosomal gene internal
      transcribed spacer (ITS) locus forward primer ITS1

<400> SEQUENCE: 12
tccgtaggtg aacctgcgg                                                19

<210> SEQ ID NO 13
<211> LENGTH: 20
<212> TYPE: DNA
<213> ORGANISM: Artificial Sequence
<220> FEATURE:
<223> OTHER INFORMATION: synthetic fungal ribosomal gene internal
      transcribed spacer (ITS) locus reverse primer ITS2

<400> SEQUENCE: 13
gctgcgttct tcatcgatgc                                               20

<210> SEQ ID NO 14
<211> LENGTH: 24
<212> TYPE: DNA
<213> ORGANISM: Artificial Sequence
<220> FEATURE:
<223> OTHER INFORMATION: synthetic fungal 28S ribosomal gene locus
      forward primer NL1

<400> SEQUENCE: 14
gcatatcaat aagcggagga aaag                                          24

<210> SEQ ID NO 15
<211> LENGTH: 19
<212> TYPE: DNA
<213> ORGANISM: Artificial Sequence
<220> FEATURE:
<223> OTHER INFORMATION: synthetic fungal 28S ribosomal gene locus
      reverse primer NL2

<400> SEQUENCE: 15
ggtccgtgtt tcaagacgg                                                19

<210> SEQ ID NO 16
<211> LENGTH: 19
<212> TYPE: DNA
<213> ORGANISM: Artificial Sequence
<220> FEATURE:
<223> OTHER INFORMATION: synthetic Staphylococcus aureus protein A (spa)
      repeat forward strand unphosphorylated primer 1095F

<400> SEQUENCE: 16
agacgatcct tcggtgagc                                                19

<210> SEQ ID NO 17
<211> LENGTH: 22
<212> TYPE: DNA
<213> ORGANISM: Artificial Sequence
<220> FEATURE:
<223> OTHER INFORMATION: synthetic Staphylococcus aureus protein A (spa)
```

```
      repeat forward strand 5'-OH phosphorylated primer
      1517R
<220> FEATURE:
<221> NAME/KEY: modified_base
<222> LOCATION: (1)...(1)
<223> OTHER INFORMATION: g modified by 5' phosphorylation

<400> SEQUENCE: 17
gcttttgcaa tgtcatttac tg                                              22

<210> SEQ ID NO 18
<211> LENGTH: 22
<212> TYPE: DNA
<213> ORGANISM: Artificial Sequence
<220> FEATURE:
<223> OTHER INFORMATION: synthetic Staphylococcus aureus protein A (spa)
      repeat forward strand unphosphorylated primer
      1517R

<400> SEQUENCE: 18
gcttttgcaa tgtcatttac tg                                              22

<210> SEQ ID NO 19
<211> LENGTH: 19
<212> TYPE: DNA
<213> ORGANISM: Artificial Sequence
<220> FEATURE:
<223> OTHER INFORMATION: synthetic Staphylococcus aureus protein A (spa)
      repeat forward strand 5'-OH phosphorylated primer
      1095F
<220> FEATURE:
<221> NAME/KEY: modified_base
<222> LOCATION: (1)...(1)
<223> OTHER INFORMATION: a modified by 5' phosphorylation

<400> SEQUENCE: 19
agacgatcct tcggtgagc                                                  19

<210> SEQ ID NO 20
<211> LENGTH: 20
<212> TYPE: DNA
<213> ORGANISM: Artificial Sequence
<220> FEATURE:
<223> OTHER INFORMATION: synthetic bacterial 16S ribosomal rRNA gene
      5'-OH phosphorylated primer 16SF
<220> FEATURE:
<221> NAME/KEY: modified_base
<222> LOCATION: (1)...(1)
<223> OTHER INFORMATION: a modified by 5' phosphorylation

<400> SEQUENCE: 20
agagtttgat cctggctcag                                                 20

<210> SEQ ID NO 21
<211> LENGTH: 15
<212> TYPE: DNA
<213> ORGANISM: Artificial Sequence
<220> FEATURE:
<223> OTHER INFORMATION: synthetic bacterial 16S ribosomal rRNA gene
      5'-OH phosphorylated primer 16SR-3
<220> FEATURE:
<221> NAME/KEY: modified_base
<222> LOCATION: (1)...(1)
<223> OTHER INFORMATION: t modified by 5' phosphorylation

<400> SEQUENCE: 21
ttaccgcggc tgctg                                                      15

<210> SEQ ID NO 22
<211> LENGTH: 18
```

```
<212> TYPE: DNA
<213> ORGANISM: Artificial Sequence
<220> FEATURE:
<223> OTHER INFORMATION: synthetic bacterial 16S ribosomal rRNA gene
      5'-OH phosphorylated primer 16SR
<220> FEATURE:
<221> NAME/KEY: modified_base
<222> LOCATION: (1)...(1)
<223> OTHER INFORMATION: t modified by 5' phosphorylation

<400> SEQUENCE: 22
ttaccgcggc tgctggca                                                    18
```